(12) United States Patent
Pekshev et al.

(10) Patent No.: US 7,498,000 B2
(45) Date of Patent: Mar. 3, 2009

(54) METHOD AND DEVICE FOR FORMING AN NO-CONTAINING GAS FLOW FOR AFFECTING A BIOLOGICAL OBJECT

(75) Inventors: Aleksandr Valerievich Pekshev, Zemledelchesky per., 14/17. str. 1, kv. 2, Moscow (RU) 119121; Andrei Borisovich Vagapov, Moskovskava (RU); Sergei Vitalievich Grachev, Moscow (RU); Nikolai Pavlovich Kozlov, Moscow (RU); Anatoly Borukhovich Shekhter, Moscow (RU)

(73) Assignee: Aleksandr Valerievich Pekshev, Moscow (RU)

( * ) Notice: Subject to any disclaimer, the term of this patent is extended or adjusted under 35 U.S.C. 154(b) by 1101 days.

(21) Appl. No.: 10/467,247

(22) PCT Filed: Feb. 1, 2002

(86) PCT No.: PCT/RU02/00032

§ 371 (c)(1),
(2), (4) Date: Jan. 22, 2004

(87) PCT Pub. No.: WO02/062412

PCT Pub. Date: Aug. 15, 2002

(65) Prior Publication Data
US 2005/0218007 A1    Oct. 6, 2005

(30) Foreign Application Priority Data
Feb. 9, 2001    (RU) ............................. 2001103924

(51) Int. Cl.
*B01J 19/08*    (2006.01)

(52) U.S. Cl. ............................. 422/186.22; 422/186.24; 204/179

(58) Field of Classification Search ............ 422/186.22, 422/186.24; 204/179
See application file for complete search history.

(56) References Cited

U.S. PATENT DOCUMENTS

| | | | |
|---|---|---|---|
| 3,666,408 A * | 5/1972 | Grosse et al. ............... | 423/405 |
| 3,903,891 A | 9/1975 | Brayshaw | |
| 4,010,897 A * | 3/1977 | Treharne et al. ............... | 239/8 |
| 4,559,206 A * | 12/1985 | Treharne et al. ....... | 422/186.24 |
| 5,396,882 A | 3/1995 | Zapol | |
| 5,950,065 A * | 9/1999 | Arlemark ................. | 422/186.2 |
| 5,993,612 A * | 11/1999 | Rostaing et al. .......... | 204/158.2 |
| 6,955,790 B2 * | 10/2005 | Castor et al. ........... | 422/186.04 |

FOREIGN PATENT DOCUMENTS

RU    2010580    4/1994

* cited by examiner

*Primary Examiner*—Kishor Mayekar
(74) *Attorney, Agent, or Firm*—Ladas & Parry LLP

(57) ABSTRACT

A method and apparatus for forming NO-containing gas flow to treat a biologic object are disclosed. The NO-containing gas flow is formed from a source gas comprising at least oxygen and nitrogen in a housing (1) comprising at least two electrodes (2,3) insulated from each other, a stationary dc arc discharge being generated and maintained between the electrodes. The NO-containing gas flow is formed from the source gas in the area between the electrodes (2,3) under the effect of the arc discharge and withdrawn through a cooled channel, enabling nitrogen oxide to be fixed in the flow and the temperature of the flow and the NO content therein to be brought to values required to provide efficient therapy of a biologic object.

35 Claims, 4 Drawing Sheets

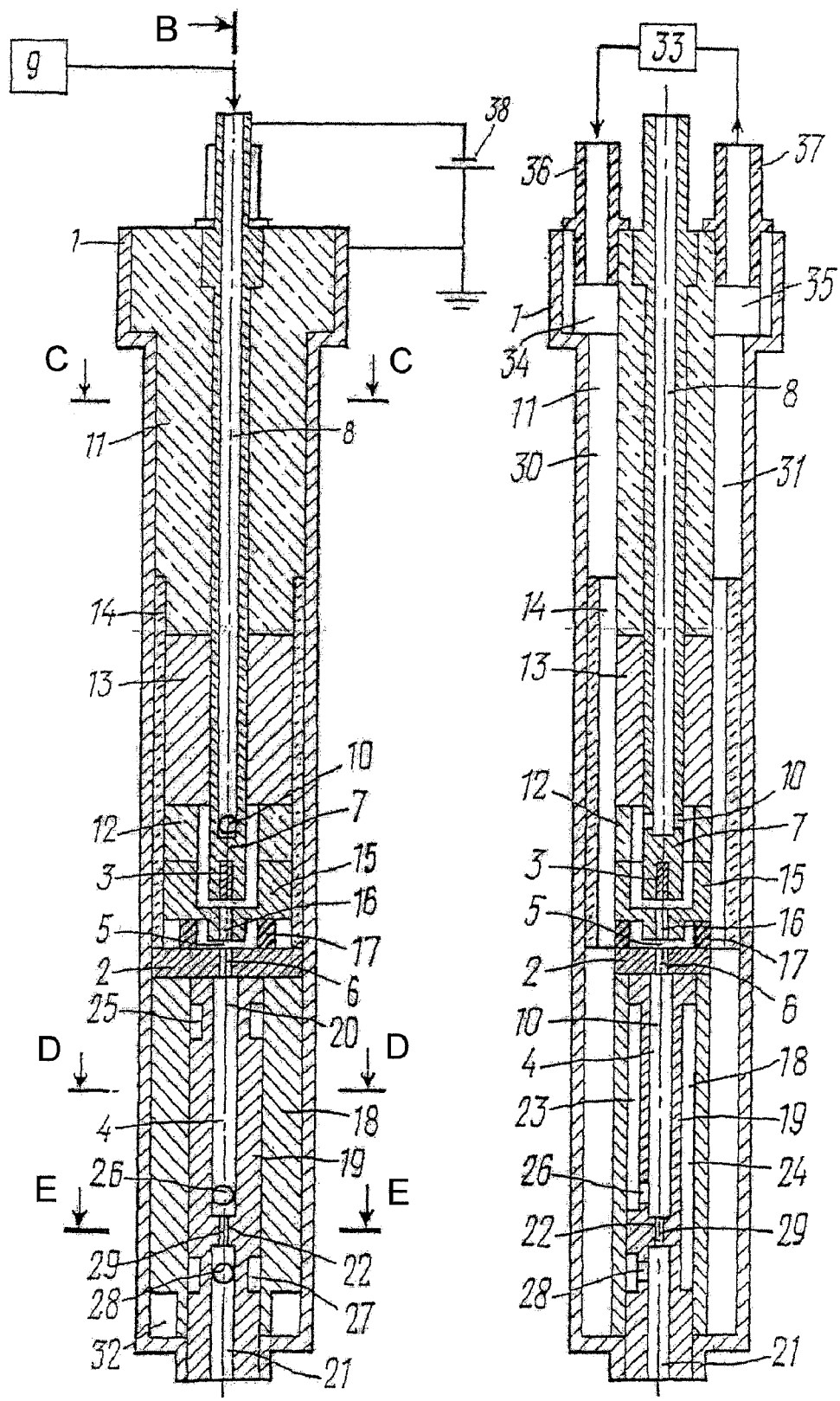

METHOD AND DEVICE FOR FORMING AN NO-CONTAINING GAS FLOW FOR AFFECTING A BIOLOGICAL OBJECT

This application is a 35 U.S.C. 371 National Stage filing of PCT/RU02/00032 on Feb. 1, 2002.

BACKGROUND OF THE INVENTION

1. Field of the Invention

The present invention relates to medical equipment and more specifically to means for providing treatment of a biological object with mixed gases containing nitrogen oxide. The invention is suitable for treating various pathological processes in general, abdominal, thoracic, purulent, vascular and anaplastic surgery, oncology, urology, combustiology, dentistry, ophthalmology, neurosurgery and other fields of medicine.

2. State of the Art

A method for preparing a mixture containing air and nitrogen oxide for treating medical pathologies by directly supplying the mixture to a certain patient's organ, taught in U.S. Pat. No. 5,396,882, Cl. A 61 M 11/00, publ. Mar. 14, 1995, comprises the steps of injecting air through an inlet channel into a spark-discharge chamber in the system; applying a high-voltage potential to a set of electrodes separated by an air gap and accommodated in the spark-discharge chamber, the high-voltage potential having an adequate peak value to generate a spark discharge in the air gap; producing a mixture of air with nitrogen oxide by the spark discharge between the electrodes under the effect of the high-voltage potential, and immediately supplying the produced air/nitrogen oxide mixture via an outlet system adapted to instantly deliver the mixed gas to a certain organ of a patient's body.

The prior art method is implemented in a system for continuously producing a mixture containing air and nitrogen oxide and intended for treating medical pathologies which need direct delivery of the mixture to an organ of a patient's body, the system comprising a spark-discharge chamber with a pair of electrodes separated by an air gap to produce nitrogen oxide by a spark discharge between the electrodes; an electric circuit for applying a high-voltage potential to the electrodes, said high-voltage potential having an adequate peak value to generate a spark discharge in the air gap; an inlet channel for supplying air into the spark-discharge chamber to produce air/nitrogen oxide mixture therein; an outlet system for directing the produced air/nitrogen oxide mixture to an organ of a patient body, the outlet system and the spark-discharge chamber being dimensioned and arranged so that to provide immediate distribution of the produced mixture from the outlet.

However, the prior art method and apparatus can be practiced only using a spark discharge as an electric discharge to produce the air/nitrogen oxide mixture.

The above method and apparatus suffer the following disadvantages:

1. Production of nitrogen oxide is intermittent because the high voltage feeding the electrical discharge is applied to the electrodes at a frequency of 50 or 60 Hz.

2. The electrodes are extremely prone to erosion which is unavoidable in spark discharges, this reducing the operation life of the apparatus and contaminating the produced air/nitrogen oxide mixture with particles of the electrode material.

3. Ozone molecules are formed in the spark discharge due to both ultra-violet radiation and impacts of electrons (since the energy of electrons is rather high) in accordance with the following reactions (where M is any reacting particle):

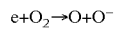
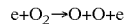
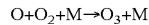

therefore, the produced mixed gas will contain ozone molecules because the spark discharge is incapable of heating gas to the temperature of ozone decomposition and turning back to oxygen.

4. The apparatus that uses a spark discharge for producing air/nitrogen oxide mixture will inevitably be a source of radio-frequency noise (both on air and in line), this causing a problem of electromagnetic compatibility with electronic equipment used in resuscitation departments and surgery rooms.

5. Restricted content of nitrogen oxide in the mixed gas produced by a spark discharge may reduce efficiency of managing some pathologic processes, such as septic and chronic wounds, necrotic injures of tissues, etc.

The aforementioned deficiencies can be overcome by the use of a stationary arc discharge supported by a high-frequency or direct current in the apparatus instead of the spark discharge, preferably by the use of a direct current (dc) discharge to alleviate the magnetic compatibility problem.

However, the use of the dc arc discharge (along with high-frequency one) is infeasible in the prior art apparatus due to the lack of a system for forced cooling of the electrodes and air/nitrogen oxide mixture produced by such discharge.

SUMMARY OF THE INVENTION

The object of the present invention is to provide a method and apparatus for forming NO-containing gas flow (NO-CGF) to treat a biologic object, which would enable, owing to the design of electrodes and outlet channel, the use of a stationary dc arc discharge to generate nitrogen oxide in an interelectrode area, as well as the outlet of the produced mixed gas from the interelectrode area at the temperature and NO concentration levels acceptable for treating a biological object and capable of providing a desired therapeutic effect.

The above object is attained in an apparatus for forming NO-containing gas flow to treat a biologic object, comprising a housing, at least two electrodes accommodated in the housing such that an interelectrode area is provided between the electrodes to generate a dc arc discharge, the electrodes being electrically insulated from each other. The apparatus further comprises voltage applying means for applying a voltage to the electrodes to generate and maintain a dc arc discharge between the electrodes, wherein a positive potential is applied to one of the electrodes, an anode, and a negative potential is applied to the other electrode, a cathode. The interelectrode area communicates with an inlet channel for injecting a source gas into the interelectrode area, the source gas containing at least oxygen and nitrogen, and an NO-containing gas flow outlet channel for withdrawing NO-containing gas flow from the interelectrode area, the outlet channel further directing the NO-containing gas flow to treat a biologic object. The NO-containing gas flow is formed in the interelectrode area from a source gas under the effect of a dc arc discharge generated and maintained between said at least two electrodes, and as the formed NO-containing gas flow passes through the outlet channel cooled by a cooling means, the nitrogen oxide content is fixed in the NO-containing gas flow and the entire flow is cooled to a temperature suitable to treat the biologic object.

The arc discharge between electrodes can be generated by providing an open-circuit dc voltage across the electrodes and forming one or a series of high-voltage pulses to generate a spark discharge between the electrodes. A value of the open-circuit voltage is selected so that to provide the change of the spark discharge to a stationary arc discharge which is maintained by a current of a predetermined value passed through the cathode to the anode throughout the operation time of the apparatus.

The above object is also attained in a method for forming NO-containing gas flow to treat a biologic object, using an apparatus comprising a housing with at least two electrodes accommodated in the housing, said electrodes being electrically insulated from each other and an interelectrode area is provided between the electrodes, and a gas flow outlet channel for withdrawing NO-containing gas flow from the interelectrode area and directing the same to treat a biologic object, the above method comprising the steps of: cooling said gas flow outlet channel and at least one of said electrodes; injecting a source gas containing at least oxygen and nitrogen into the interelectrode area, and generating and maintaining a dc arc discharge between said at least two electrodes in the interelectrode area to form NO-containing gas flow; passing the NO-containing gas flow through the gas flow outlet channel in order to fix the content of nitrogen oxide in the NO-containing gas flow and cool the flow to a temperature suitable to treat the biologic object.

The arc discharge between the electrodes is generated by providing an open-circuit dc voltage across the electrodes and generating at least one high-voltage pulse to generate a spark discharge between the electrodes, a value of the open-circuit voltage being selected so that to provide the change of the spark discharge to a stationary arc discharge, wherein the open-circuit voltage is at least 400 V, and the high pulse voltage is at least 5 kV.

Furthermore, the stationary dc arc discharge is maintained by a current of preferably at least 2.3 A, the arc discharge being stabilized using an arc discharge stabilization electrode to provide steady generation of air plasma with a predetermined temperature in the interelectrode area.

The source gas is preferably ambient air at a flow rate in the range from 1 to 4 liters per minute, and the cooling agent is a mixture of distilled water with ethyl alcohol at a flow rate in the range from 1.5 to 2 liters per minute.

A portion of an NO-containing gas flow outlet channel according to the present invention may be non-rectilinear, Said non-rectilinear portion may have a shape such as labyrinth, spiral, volute, Also, an outlet channel of the present invention may have a varying cross-sectional area.

BRIEF DESCRIPTON OF THE DRAWINGS

The present invention will become apparent from the following detailed description of preferred embodiments with reference to the accompanying drawings, in which:

FIG. 1 is a general longitudinal sectional view of a manual embodiment (held in hand when used) of an apparatus for forming NO-CGF to treat a biologic object, in accordance with the invention;

FIG. 2 is the same apparatus shown in a section through line B-B in FIG. 1, in accordance with the invention;

DESCRIPTION OF PREFERRED EMBODIMENTS OF THE INVENTION

Figure 3:
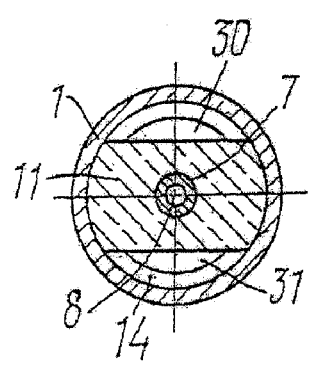
FIG. 3 is the same apparatus shown in a section through line C-C in FIG. 1, in accordance with the invention.
Figure 4:
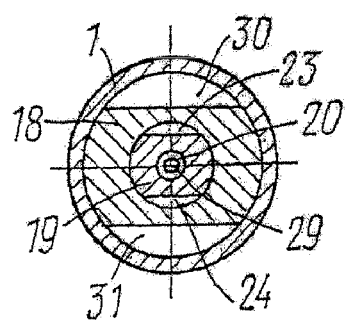
FIG. 4 is the same apparatus shown in a section through line D-D in FIG. 1, in accordance with the invention.
Figure 5:
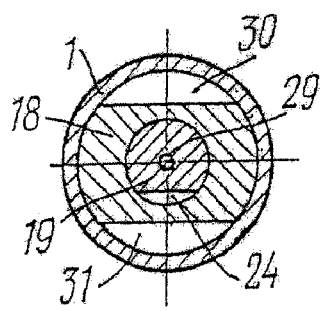
FIG. 5 is the same apparatus shown in a section through line E-E in FIG. 1, in accordance with the invention.
Figure 6:
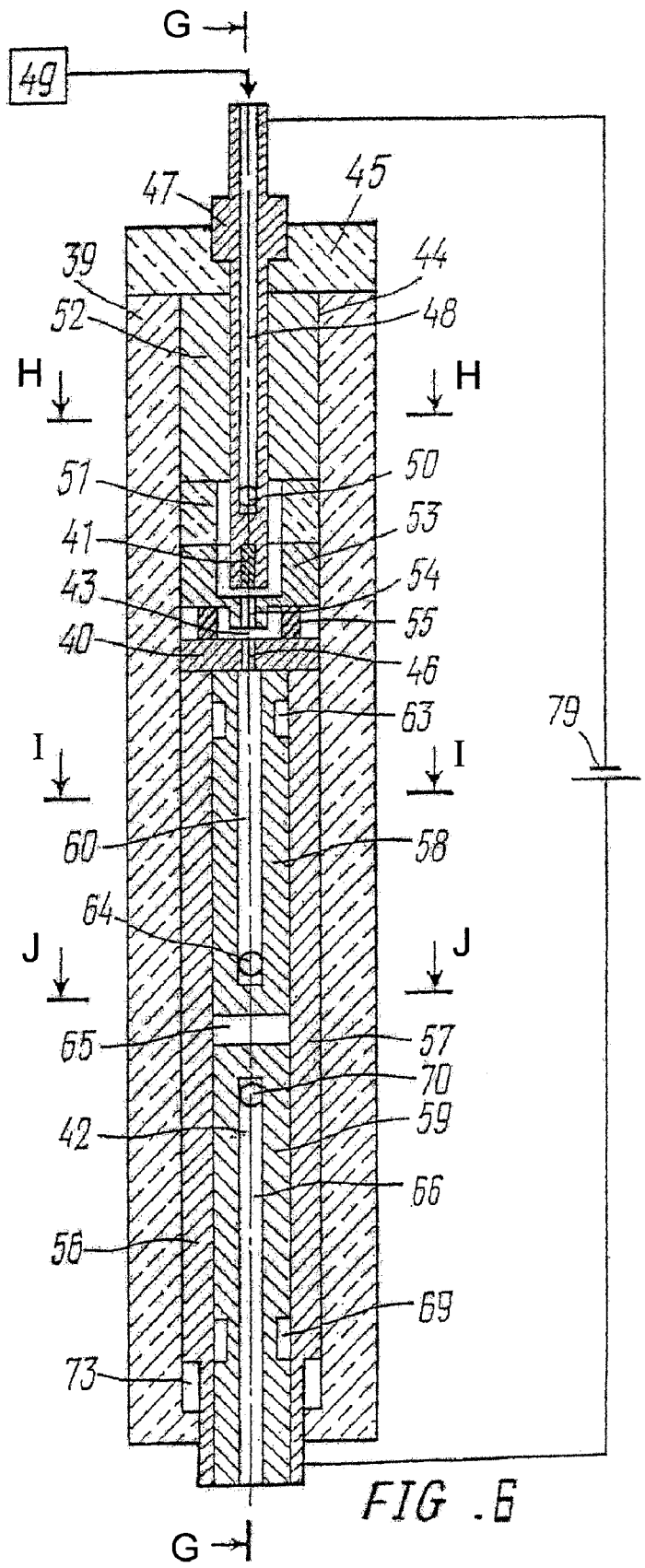
FIG. 6 is a general longitudinal sectional view of a stationary embodiment of an apparatus for forming NO-CGF to treat a biologic object, in accordance with the invention.
Figure 7:
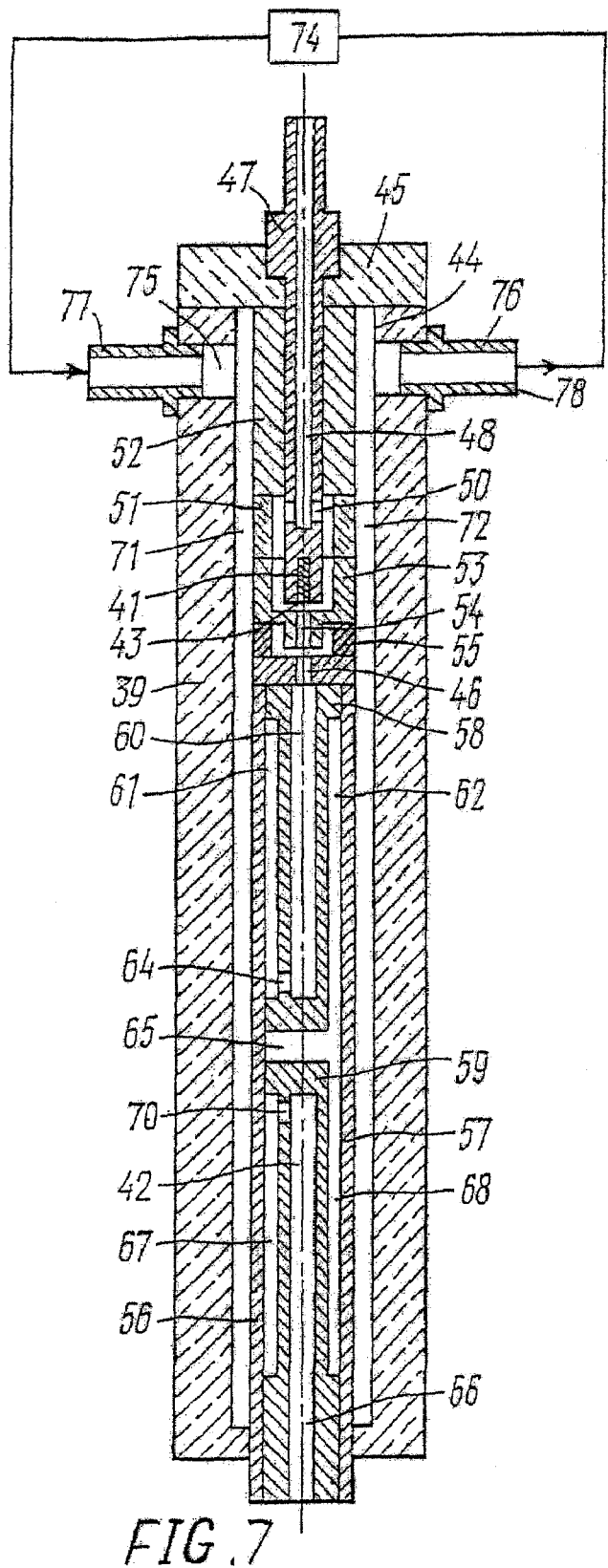
FIG. 7 is the same apparatus shown in a section through line G-G in FIG. 6, in accordance with the invention.
Figure 8:
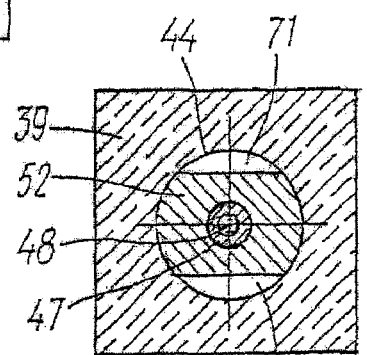
FIG. 8 is the same apparatus shown in a section through line H-H in FIG. 6, in accordance with the invention.
Figure 9:
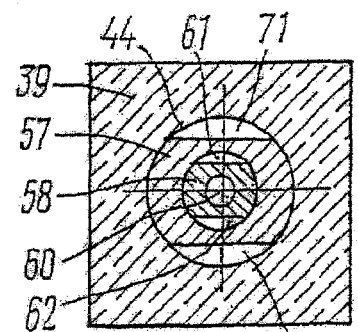
FIG. 9 is the same apparatus shown in a section through line I-I in FIG. 6, in accordance with the invention.
Figure 10:
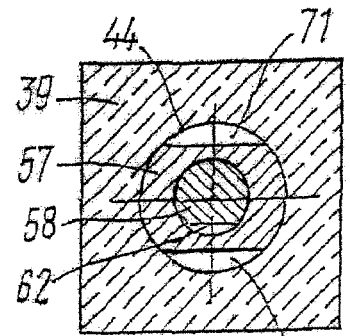
FIG. 10 is the same apparatus shown in a section through line J-J in FIG. 6, in accordance with the invention.

Referring to FIGS. 1 to 5, an apparatus in accordance with the invention comprises a thin-wall cylinder housing 1 made of a conductive material, an anode 2 electrically coupled to the housing, a cathode 3 and an NO-containing gas flow outlet channel 4 for withdrawing NO-containing gas flow from an interelectrode area 5.

The anode 2 is made of tin bronze in the shape of a cylinder disk with an axial through hole 6 coaxial with an input of the NO-containing gas flow outlet channel 4, the anode being electrically coupled to the channel.

The cathode 3 is coaxially arranged in the housing 1 and flush pressed in a cylinder cathode holder 7 made of an electrically and heat conducting material, such as copper. Inside the cathode holder 7 there is provided a cylinder channel 8 which is connected on one side to a pump 9 for injecting a source gas, and communicates on the other side with the interelectrode area 5 via radial openings 10. The cathode 3 is a thermochemical cathode made of a material of Group IV, titanium subgroup IV B of the Periodic Table, e.g. hafnium.

The cathode holder 7 is coaxially mounted in the housing 1 with the aid of an insulating insert 11 made of a dielectric material, such as organic glass.

A radiator 13 is coaxially mounted in the housing 1 between the insulating insert 11 and an insulating sleeve 12 to extract heat from the cathode holder 7, the radiator being in the shape of a sleeve of a heat-conducting material, such as copper, and embracing the cylinder surface of the cathode holder 7 in the immediate vicinity of the cathode 3 with minimum radial clearances to provide optimal thermal contact between them. To prevent electrical contact between the radiator 13 which is under the cathode's potential and the housing 1 which is under the anode's potential, the apparatus comprises a thin-wall cylinder shield 14 made of a dielectric material, such as organic glass, and mounted coaxially between the radiator 13 and the housing 1.

An electrode 15 with a cylindrical through hole 16 is coaxially located in the interelectrode area 5 between the cathode 3 and anode 2, the electrode 15 being intended for stabilization of the arc discharge and made of an electrically and heat conducting material, e.g. copper; the arc discharge stabilization electrode is electrically insulated from the cathode and the anode by the insulating sleeve 12, the thin-wall cylindrical shield 14 and a dielectric, preferably high-temperature seal 17, e.g. of silicone resin.

The NO-containing gas flow outlet channel 4 is formed by an external and internal cylindrical sleeves 18 and 19, respectively, both made of a heat-conducting material, such as copper, and coaxially disposed in the housing 1. The channel 4 comprises an axial cylinder nitrogen oxide "quench" chamber 20 and an axial cylinder gas outlet 21 separated by a transverse partition 22. The chamber 20 and the outlet 21 are connected by a gas flow cooling path comprised of diametrically opposite channels 23 and 24 (FIGS. 2,4,5) connected by an annular bore 25 (FIG. 1), the channel 23 being connected to the nitrogen oxide "quench" chamber 20 through a radial opening 26, and the channel 24 being connected to the gas outlet 21 through an annular bore 27 (FIG. 1) and a radial opening 28.

To form an axial light spot, a cylinder through channel 29 of a small diameter (0.6-0.8 mm) may be formed in the center of the partition 22.

The external cylinder surfaces of the insulating insert 11, radiator 13, insulating sleeve 12 of the arc discharge stabilization electrode 15, anode 2, external sleeve 18 of the NO-containing gas flow outlet channel 4 are provided with two diametrically opposite flats (FIGS. 2 to 5) which form channels 30 and 31 with the cylinder surface of the housing 1, the channels 30 and 31 being connected therebetween by an annular cavity 32 (FIG. 2) and intended for circulation of a cooling agent within the system, the cooling agent being injected and discharged by a pump 33 through cylinder channels 34 and 35 (FIG. 2) connected with cooling agent supply and discharge nipples 36 and 37, respectively.

The cooling agent is preferably a mixture of distilled water with ethyl alcohol, e.g. in the 50:50 ratio (by volume).

Supply voltage is applied to the anode 2 by connecting the housing 1 to a positive terminal, and to the cathode 3 by connecting the cathode holder 7 to a negative terminal of a power source 38.

Another embodiment of an apparatus in accordance with the present invention is illustrated in FIGS. 6 to 10. The apparatus comprises a housing 39 made of a dielectric material, an anode 40, a cathode 41 and an NO-containing gas flow outlet channel 42 for withdrawing the NO-containing gas flow from an interelectrode area 43.

The housing 39 made of e.g. organic glass has an axial cylinder cavity 44 and a sealed closure 45.

The anode 40 is made of tin bronze in the shape of a cylinder disc with an axial through hole 46 coaxial with an inlet of the NO-containing gas flow outlet channel 42, the anode being electrically coupled to the above channel.

The cathode 41 is arranged along the axis of the housing 39 and flush pressed in a cylinder cathode holder 47 made of an electrically and heat conducting material, such as copper. Inside the cathode holder 47 there is provided a cylinder channel 48 connected on one side to a source gas supply pump 49 and communicating on the other side (via radial openings 50) with an interelectrode area 43. The cathode 41 is a thermochemical cathode made of a material of Group IV, titanium subgroup IV B of the Periodic Table, such as hafnium.

The cathode holder 47 is mounted along the axis of the housing 39 with the aid of the closure 45 which may be made of any material.

A radiator 52 is mounted in the housing 39 coaxially with the closure 45 and an insulating sleeve 51 to extract heat from the cathode holder 47, the radiator being in the shape of a sleeve made of a heat conducting material, such as copper, and embracing the cylinder surface of the cathode holder 47 in the immediate vicinity of the cathode 41 with minimum radial clearances to provide optimal thermal contact between them.

An arc discharge stabilization electrode 53 having a cylinder through hole 54 and made of an electrically and heat conducting material, such as copper, is coaxially arranged between the cathode 41 and anode 40 in the interelectrode area 43 and electrically insulated from them by an insulating sleeve 51 and a dielectric, preferably high-temperature seal 55 made of a silicone resin, respectively.

The NO-containing gas flow outlet channel 42 for withdrawing the NO-containing gas flow from the interelectrode area has two stages and is made inside an insert 56 comprised of one external cylinder sleeve 57 and two internal cylinder sleeves 58 and 59 made of an electrically and heat conducting material, such as copper, and arranged coaxially in the housing 39. The first stage of the channel comprises an axial cylinder nitrogen oxide "quench" chamber 60 and an intermediate gas flow cooling path comprised of diametrically opposite channels 61 and 62 connected through an annular bore 63 (FIG. 6), the channel 61 being connected to the nitrogen oxide "quench" chamber 60 through a radial opening 64, and the channel 62 being connected to a area of a thermal isolation chamber 65.

The second stage of said channel comprises an axial cylinder gas outlet 66 and a final gas flow cooling path comprised of diametrically opposite channels 67 and 68 connected therebetween through an annular bore 69 (FIG. 6), the channel 68 being connected with the area of the thermal isolation chamber 65, and the channel 67 being connected with the gas outlet 66 via a radial opening 70.

Two diametrically opposite flats are provided on the external cylinder surfaces of the radiator 52, insulating sleeve 51, arc discharge stabilization electrode 53, anode 40, external sleeve 57 of the insert 56 in which the NO-containing gas flow outlet channel is made (FIGS. 7 to 10); the flats form with the internal cylinder surface of the housing 39 channels 71 and 72 connected through an annular cavity 73 (FIG. 6) and adapted to provide circulation, in the cooling system, of a cooling agent which is injected and discharged by a pump 74 through cylindrical channels 75 and 76 connected to cooling agent supply and discharge nipples 77 and 78.

The cooling agent is preferably a mixture of distilled water with ethyl alcohol, e.g. in the 50:50 ratio (by volume).

The supply voltage is applied to the anode 40 by connecting the insert 56 to a positive terminal, and to the cathode 41 by connecting the cathode holder 47 to a negative terminal of the power source 79.

The apparatus shown in FIGS. 1 to 5 is generally adapted to treat wound pathology, being held in user's hand when in use, and operates as follows.

Prior to operation, the apparatus is connected to flexible hydro-gas lines 1.5 m in length which switch the apparatus to the power source 38 located in a service unit (not shown), a cooling agent pump 33 and a source gas supply pump 9, the source gas being ambient air.

The cooling agent is supplied at a flow rate of from 1.5 to 2.0 l/min through the nipple 36 and the cylinder channel 34 to the channel 30 and passed over the channel 30 along the radiator 13, arc discharge stabilization electrode 15, anode 2, NO-containing gas flow outlet channel 4 to cool them, and then discharged from the apparatus via the annular cavity 32, diametrically opposite channel 31, cylinder channel 35 and nipple 37.

The integration of the cooling systems of the cathode 3 (by cooling the radiator 13 and cathode holder 7), the arc discharge stabilization electrode 15, the anode 2 and the NO-containing gas flow outlet channel 4 in a single hydraulically connected system enables the heat to be efficiently removed from all of the listed structural components at small lateral dimensions of the apparatus and a low flow rate of a cooling agent, this ensuring the operational capability and long life of the components, as well as keeping a "comfortable" temperature for user's hand at the external surface of the housing 1.

The service unit comprises cooling system testing means for testing at least the ability to work and air-tightness of the system. When the testing means outputs a cooling system perfect state signal, a working gas, ambient air, is supplied and the power source of the apparatus is switched on at the same time.

The source gas at a flow rate of from 1 to 4 l/min is injected through the cylinder channel 8 and radial openings 10 in the cathode holder 7 into the interelectrode area 5, the axial hole 6 in the anode 2 and the NO-CGF outlet channel 4.

Figure 11:
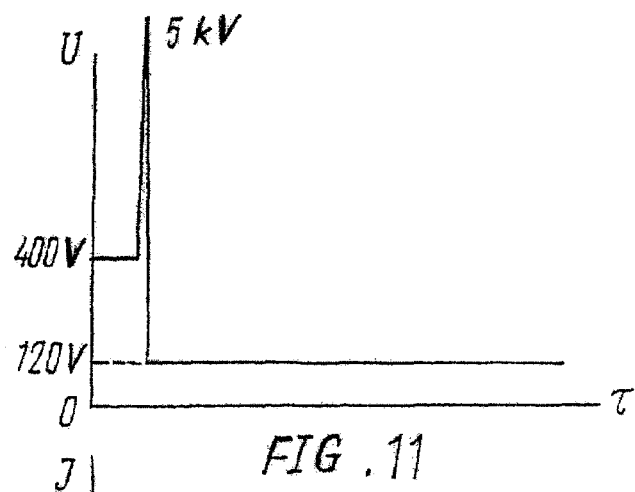
FIG. 11 is a schematic representation of levels and waveforms of the electric voltage feeding an apparatus for forming NO-CGF to treat a biologic object, in accordance with the invention.
Figure 12:
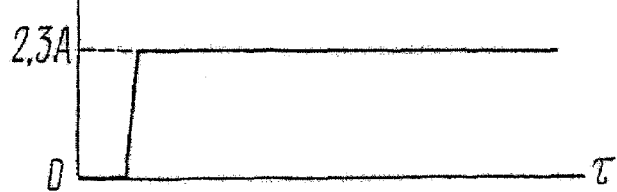
FIG. 12 is a schematic representation of levels and waveforms of the electric current consumed by an apparatus for forming NO-CGF to treat a biologic object, in accordance with the invention.

Simultaneously with the source gas injection, a dc voltage of about 400 V is applied to the housing 1 and the cathode holder 7, the voltage value being insufficient to generate a discharge in the interelectrode area. The voltage is referred to as an open-circuit voltage. Then, a high pulse voltage of about 5 kV is applied from the power source to the electrodes to initiate a spark discharge between an end face of the cathode holder 7 with the cathode 3 pressed therein and the internal cylinder surface of the hole 6 in the anode 2. Generally, one high voltage pulse is sufficient to initiate a spark discharge. Under the effect of the open-circuit voltage the spark discharge changes to a stationary arc discharge with a current of the order of 2.3 A and a voltage of the order of 120 V, that are provided by geometrical dimensions of the electrodes and the power source characteristics. The process characteristics are illustrated in FIGS. 11 and 12. If the spark discharge has failed to change to a stationary arc discharge upon the first high voltage pulse, the next pulse is supplied from the power source.

The arc discharge stabilization electrode 15, being under the "floating" potential, fixes the average arc length, thereby providing a steady discharge burning along the arc length that is greater than the self-adjusting arc length, and prevents development of a bridging process, therefore, a steady generation of air plasma at a temperature of from 3500 to 4000 K is provided in the interelectrode area at given flow rates of the source gas, the plasma being optimal to effect the nitrogen oxide synthesis therein in accordance with the plasma-chemical reaction:

$$N_2+O_2 \leftrightarrows 2NO-180.9 \text{ kJ}.$$

The air/plasma flow having a temperature of from 3000 to 3500 K and a nitrogen oxide content of about 4-5% is supplied from the axial hole 6 in the anode 2 to the axial cylinder nitrogen oxide "quench" chamber 20, at the initial part of which the flow is fast cooled to a temperature of about 1000 K, thereby fixing the nitrogen oxide synthesized in the plasma discharge in the gas flow. The gas flow then passes from the "quench" chamber 20 via the radial opening 26 over the cooling channels 23 and 24, via the radial opening 28 to the gas outlet 21 and outside.

Figure 13:
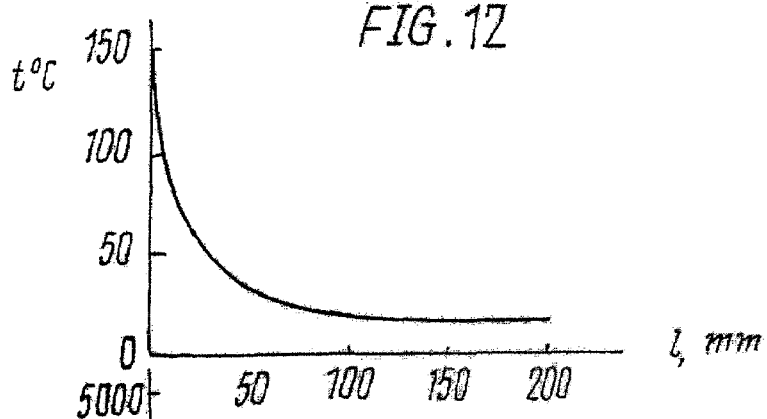
FIG. 13 is a schematic representation of gas temperature distribution along the centerline of the NO-CGF formed by an apparatus shown in FIGS. 1 to 5, in accordance with the invention.

The shape and geometrical dimensions of the NO-containing gas flow outlet channel 4 are such that the gas flow axial temperature at exit of the outlet 21 is about 150° C. and sufficiently fast drops to a room temperature as the flow moves away from the exit of the outlet 21 (FIG. 13). This permits not only the nitrogen oxide, but the heat component of the gas flow to be also used for treatment when necessary, e.g. for coagulation of diffused bleeding in wound pathology.

Figure 14:
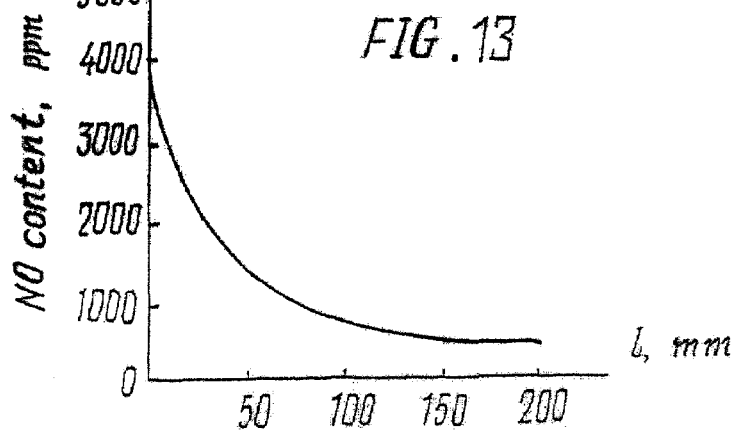
FIG. 14 is a schematic representation of nitrogen oxide content (concentration) along the centerline of the NO-CGF formed by an apparatus shown in FIGS. 1 to 10, in accordance with the invention.

FIG. 14 graphically shows the nitrogen oxide content on the gas flow axis against the distance from the exit of the outlet 21.

When treating a biological object, the gas flow axis is imaged by a light spot formed by a cylinder through orifice 29 in the center of the partition 22, through which the radiated emission partly passes from the interelectrode area 5.

The apparatus shown in FIGS. 6 to 10 is intended for therapy of various pathologies by an NO-containing gas flow cooled substantially to the cooling agent temperature. The apparatus is stationary built-in in a service unit, connected to the power source 79 located therein, the cooling agent pump 74 and the operating gas supply pump 49, the operating gas being ambient air, and operates as follows.

A cooling agent is supplied at a flow rate of 1.5 to 2.0 l/min through the nipple 77 and the cylinder channel 75 to the channel 71 over which it flows along the radiator 52, arc discharge stabilization electrode 53, anode 40, NO-gas flow outlet channel 42 to cool them and is discharged from the apparatus via the annular cavity 73, diametrically opposite channel 72, cylinder channel 76 and nipple 78.

The service unit comprises cooling system testing means to test at least the ability to work and air-tightness of the system. When the testing means outputs a cooling system perfect state signal, a working gas, ambient air, is supplied and the power source of the apparatus is switched on at the same time.

The source gas is supplied at a flow rate of from 1 to 4 l/min via the cylinder channel 48 and the radial openings 50 in the cathode holder 47 into the interelectrode area 43 and then to the axial hole 46 in the anode 40 and to the NO-CGF outlet channel 42.

Simultaneously with the source gas supply, a direct voltage of the order of 400 V (open-circuit voltage) and a high pulse voltage of the order of 5 kV are applied from the power source to the insert 56 and the cathode holder 47, the high pulse voltage initiating a spark discharge between an end face of the cathode holder 47 with the cathode 41 pressed therein and the internal cylinder surface of the hole 46 in the anode 40. Under the effect of the open-circuit voltage, the spark discharge changes to a stationary arc discharge with a current of the order of 2.3A and a voltage of the order of 120V that are provided by geometrical dimensions of the electrodes and the power source characteristics (see FIGS. 11, 12). The arc discharge stabilization electrode 53, being under the "floating" potential, fixes the average arc length thereby providing a steady discharge burning at the arc length greater that the self-adjusting arc length, and prevents development of a bridging process, therefore, a steady generation of air plasma at a temperature of from 3500 to 4000 K is provided in the interelectrode area at given flow rates of the source gas, the plasma being optimal to effect the nitrogen oxide synthesis therein in accordance with the plasma-chemical reaction:

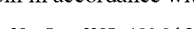

$$N_2+O_2 \leftrightarrows 2NO-180.9 \text{ kJ}.$$

The air/plasma flow having a temperature of from 3000 to 3500 K and a nitrogen oxide content of about from 4 to 5% is supplied from the axial hole 46 in the anode 40 into the axial cylinder nitrogen oxide "quench" chamber 60, at the initial part of which the flow is fast cooled to a temperature of about 1000 K, this fixing the nitrogen oxide synthesized in the plasma discharge in the gas flow. The gas flow then passes from the "quench" chamber 60 via the radial opening 64 over the channels 61 and 62 of the intermediate cooling path and at a temperature of about 150° C. enters the thermal isolation chamber 65. From the chamber the gas flow passes into the channels 68 and 67 of the final cooling path and, via the radial opening 70, to the axial cylinder outlet 66.

The shape and geometrical dimensions of the NO-containing gas flow outlet channel 42 are such that the gas flow leaves the channel. 66 cooled to a room temperature of from 20 to 25° C., this enabling its delivery through a flexible pipe (not shown) made e.g. of silicone and connected to the outlet 66 to substantially any biological object.

An apparatus for forming NO-containing gas flow (NO-CGF) to treat a biological object in accordance with the present invention is applicable in various fields of medicine: oncology and military surgery, contaminated surgery, pulmonology and thoracic surgery, traumatology and orthopedics, ophthalmology, dentistry, gynecology, urology, dermatology, etc.

Available data testify that the use of NO-CGF proved to be highly efficient in therapy of purulent and persistent wounds, gunshot and mine explosion injuries, radiation and trophic ulcers, diabetic foot syndrome, pressure sores and burns, parodentium diseases, uterine appendage suppurative inflammations and pseudo-erosions of neck of uterus, as well as in the complex therapy of noninfectious pleural empyema and nonspecific sustained inflammatory pneumonic diseases.

The apparatus in accordance with the present invention may be used in combination with endoscope instruments and biopsy needles, this showing promise for the apparatus employment in managing gastric and stomal ulcers, peritonitis, mastitis, prostatitis, joint diseases, tumor processes, etc. In addition, the intact skin permeability to NO-CGF may enable the use of the apparatus in treatment of regional vascular and nervous diseases.

Those skilled in the art will recognize that a variety of modifications and additions may be made to the apparatus and method without departing from the spirit of the invention. Accordingly, the invention should not be deemed limited to the particular constructions and steps as set out in detail above and in the accompanying drawings, but instead only by a fair scope of the claims that follow along with their equivalents.

What is claimed is:

1. An apparatus for forming NO-containing gas flow to treat a biologic object, the apparatus comprising:
    a housing;
    at least two electrodes accommodated inside said housing so that an interelectrode area is provided between said electrodes to generate a direct current arc discharge, said electrodes being electrically insulated from each other;
    voltage applying means for applying a voltage to said electrodes to generate and maintain the direct current arc discharge between the electrodes, wherein a positive potential is applied to one of the electrodes being an anode, and a negative potential is applied to another electrode being a cathode;
    floating potential electrode disposed in said interelectrode area, electrically insulated from said anode and said cathode, wherein said floating potential electrode has a through hole coaxial with the cathode to provide a steady discharge burning;
    an inlet channel communicating with said interelectrode area for injecting source gas into the interelectrode area, said source gas containing at least oxygen and nitrogen;
    an NO-containing gas flow outlet channel for withdrawing NO-containing gas flow from the interelectrode area and directing said NO-containing gas flow to treat the biologic object, said NO-containing gas flow being formed from said source gas under the effect of said direct current arc discharge, and
    cooling means for cooling said outlet channel and at least one of said anode and cathode.

2. The apparatus according to claim 1, further comprising a pump for supplying the source gas into the inlet channel.

3. The apparatus according to claim 1, wherein at least one of said channels is provided within said housing.

4. The apparatus according to claim 1, wherein at least a portion of said outlet channel is non-rectilinear.

5. The apparatus according to claim 4, wherein said non-rectilinear portion of the outlet channel has a shape selected from a group including labyrinth, spiral and volute.

6. The apparatus according to claim 1, wherein said outlet channel has a varying cross-sectional area.

7. The apparatus according to claim 6, wherein said outlet channel comprises at least one partition with an orifice, an area of said orifice being substantially less than an area of said outlet channel.

8. The apparatus according to claim 1, wherein said cathode is mounted in a cathode holder, said inlet channel being formed in said cathode holder.

9. The apparatus according to claim 8, wherein said cathode holder is mounted in the housing with the aid of an insert of a dielectric material.

10. The apparatus according to claim 8, further comprising a radiator disposed within the housing to remove heat from the cathode holder, said radiator at least partly embracing an external surface of the cathode holder and insulated from the floating potential electrode and the housing.

11. The apparatus according to claim 10, wherein said radiator is made of copper, and a shield of a dielectric material is mounted between the radiator and the housing.

12. The apparatus according to claim 8, wherein said cathode holder is made of copper.

13. The apparatus according to claim 8, wherein said cathode is thermochemical and pressed in the cathode holder.

14. The apparatus according to claim 13, wherein said thermochemical cathode is made of a material of Group IV of the Periodic Table.

15. The apparatus according to claim 14, wherein said thermochemical cathode is made of hafnium.

16. The apparatus according to claim 1, wherein said anode has a hole through which said outlet channel communicates with the interelectrode area.

17. The apparatus according to claim 16, wherein the through hole of the floating potential electrode is coaxial with the cathode and the through hole in the anode.

18. The apparatus according to claim 17, wherein said cathode and said holes in the anode and the floating potential electrode are cylindrical, the hole in the floating potential electrode having a diameter greater than or equal to a diameter of the cathode, and less than or equal to a diameter of the hole in the anode.

19. The apparatus according to claim 1, wherein said housing is made of a conductive material and electrically coupled to said anode.

20. The apparatus according to claim 1, wherein said floating potential electrode is mounted with a gap relative to the cathode and insulated from said housing and said anode by a shield of a dielectric material and a dielectric seal, respectively.

21. The apparatus according to claim 1, wherein said housing is made of a dielectric material and further comprises an insert made of an electrically and heat conducting material and electrically connected to the anode, said NO-containing gas flow outlet channel being formed in the insert.

22. The apparatus according to claim 21, wherein said floating potential electrode is mounted with a gap relative to the cathode and insulated by a dielectric seal from the anode.

23. The apparatus according to claim 21, wherein said cathode is mounted in a cathode holder, said inlet channel being formed in said cathode holder, and further comprising a radiator disposed within the housing to extract heat from the cathode holder, said radiator at least partly embracing an external surface of the cathode holder and insulated from the floating potential electrode.

24. The apparatus according to claim 23, wherein said radiator is made of copper.

25. The apparatus according to claim 1, wherein said cooling means comprises channels made in the housing for circulation of a cooling agent.

26. The apparatus according to claim 25, further comprising a pump for forced circulation of the cooling agent.

27. The apparatus according to claim 25, wherein said source gas is ambient air, and said cooling agent is a mixture of distilled water with ethyl alcohol.

28. The apparatus according to claim 1, wherein said floating potential electrode is made of copper.

29. A method for forming NO-containing gas flow to treat a biologic object, the method comprising the following steps:
providing a housing with at least two electrodes accommodated within the housing, said electrodes being electrically insulated from each other and an interelectrode area is provided between the electrodes;
providing a floating potential electrode disposed in said interelectrode area and electrically insulated from said at least two electrodes;
providing a gas flow outlet channel for withdrawing NO-containing gas flow from the interelectrode area and directing said NO-containing gas flow to treat a biologic object;
cooling said gas flow outlet channel and at least one of said electrodes;
injecting a source gas containing at least oxygen and nitrogen into the interelectrode area, and generating and maintaining a direct current arc discharge between said at least two electrodes in the interelectrode area to form the NO-containing gas flow, while providing a steady discharge burning with said floating potential electrode to fix a content of nitrogen oxide in the NO-containing gas flow and cool the flow to a temperature suitable to treat the biologic object, and passing said NO-containing gas flow over said gas flow outlet channel.

30. The method according to claim 29, wherein said arc discharge between electrodes is generated by providing an open-circuit direct current voltage across the electrodes and forming at least one high voltage pulse to generate a spark discharge between the electrodes, a value of the open-circuit voltage being selected such that to provide a change of the spark discharge to a stationary arc discharge.

31. The method according to claim 30, wherein said open-circuit voltage is at least 400 V, and said high pulse voltage is at least 5 kV.

32. The method according to claim 29, wherein said stationary direct current arc discharge is maintained by a current of at least 2.3 A.

33. The method according to claim 29, wherein said source gas is ambient air.

34. according to claim 29, wherein said cooling agent is a mixture of distilled water with ethyl alcohol at a flow rate in a range from 1.5 to 2 liters per minute.

35. The method according to claim 29, wherein a flow rate of the source gas is in a range from 1 to 4 liters per minute.

* * * * *